(12) United States Patent
Azam et al.

(10) Patent No.: US 10,112,876 B2
(45) Date of Patent: Oct. 30, 2018

(54) PROCESS FOR OLIGOMERIZATION OF ETHYLENE

(71) Applicants: Saudi Basic Industries Corporation, Riyadh (SA); Linde AG, Munich (DE)

(72) Inventors: Shahid Majeed Azam, Riyadh (SA); Abduljelil Iliyas, Riyadh (SA); Abdullah Mohammad Alqahtani, Riyadh (SA); Shehzada Khurram, Riyadh (SA); Anina Wöhl, Munich (DE); Wolfgang Müller, Munich (DE); Marco Harff, Munich (DE); Andreas Meiswinkel, Prien (DE); Heinz Bölt, Wolfratshausen (DE)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 91 days.

(21) Appl. No.: 14/125,805

(22) PCT Filed: Sep. 5, 2013

(86) PCT No.: PCT/EP2013/002670
§ 371 (c)(1),
(2) Date: Dec. 12, 2013

(87) PCT Pub. No.: WO2014/082689
PCT Pub. Date: Jun. 5, 2014

(65) Prior Publication Data
US 2015/0299069 A1    Oct. 22, 2015

(30) Foreign Application Priority Data
Nov. 28, 2012 (EP) .................................... 12194589

(51) Int. Cl.
C07C 2/24 (2006.01)
C07C 2/34 (2006.01)
C07C 2/36 (2006.01)

(52) U.S. Cl.
CPC .................. *C07C 2/34* (2013.01); *C07C 2/36* (2013.01); *C07C 2531/18* (2013.01);
(Continued)

(58) Field of Classification Search
CPC ... C07C 2/34; C07C 2531/18; C07C 2531/22; C07C 2/08; C07C 2/36
(Continued)

(56) References Cited

U.S. PATENT DOCUMENTS 5,853,551 A    12/1998  Boucot et al.
6,858,767 B1 * 2/2005  DiMaio .................. C08F 10/00
                                                           585/511
(Continued)

FOREIGN PATENT DOCUMENTS

EP      2106854 A1    10/2009
JP      H11199357 A    7/1999
WO      2011112184 A1   9/2011

OTHER PUBLICATIONS

Extended European Search Report for European Application No. 12194589.3-2109; dated Jan. 24, 2013; 4 pages.
(Continued)

*Primary Examiner* — In Suk C Bullock
*Assistant Examiner* — Aaron W Pierpont
(74) *Attorney, Agent, or Firm* — Cantor Colburn LLP

(57) ABSTRACT

The present invention relates to a process for the oligomerization of ethylene, comprising: a) oligomerization of ethylene in a reactor in the presence of solvent and catalyst; b) transferring reactor overhead effluent to an externally located cooling device and recycling condensed effluent into
(Continued)

Figure 1:
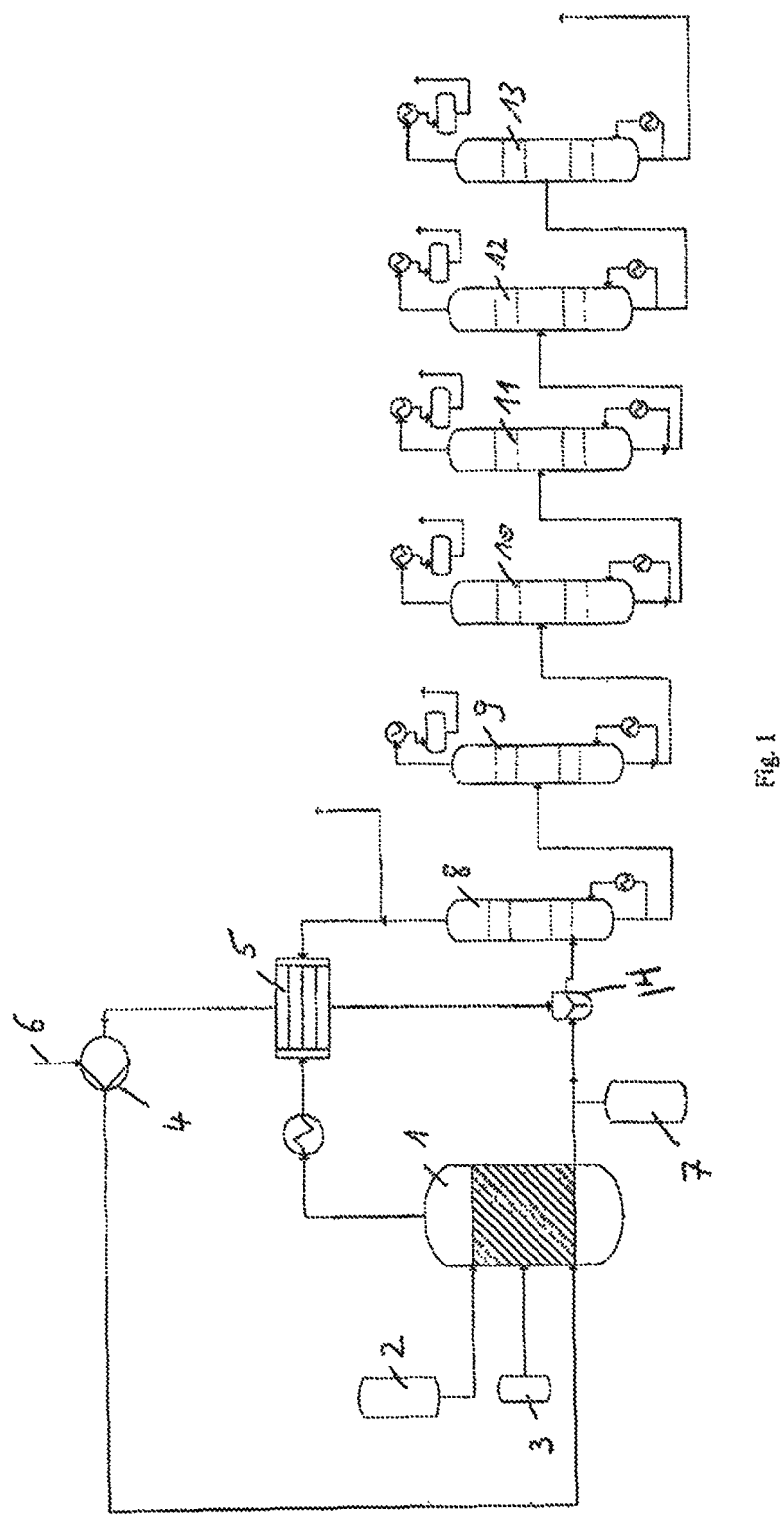

the reactor; c) transferring the reactor bottom effluent to a series of fractionation columns and, in the following order, i) optionally separating a C4 fraction, ii) separating a C6 fraction, iii) simultaneously separating C8 and C10 fractions and recycling thereof into the reactor, and iv) separating residues comprising ≥C12 fractions, spent catalyst polymer material and quench media, from the process, wherein the solvent is separated in any of the steps i)-iv) and/or in an additional step.

12 Claims, 2 Drawing Sheets

(52) U.S. Cl.
CPC ...... *C07C 2531/20* (2013.01); *C07C 2531/22* (2013.01); *C07C 2531/34* (2013.01)

(58) Field of Classification Search
USPC .................. 585/513, 522, 500, 502, 510
See application file for complete search history.

(56) References Cited

U.S. PATENT DOCUMENTS

| | | |
|---|---|---|
| 2006/0254131 A1* | 11/2006 | Waters .................. C10L 1/1641 44/459 |
| 2007/0185358 A1 | 8/2007 | Buchanan et al. |
| 2007/0185362 A1* | 8/2007 | Lattner ..................... C07C 2/32 585/521 |
| 2010/0190939 A1* | 7/2010 | Fritz ..................... B01J 31/143 526/126 |
| 2011/0172370 A1 | 7/2011 | Aliyev et al. |
| 2012/0029258 A1 | 2/2012 | Wohl et al. |
| 2015/0203418 A1 | 7/2015 | Meiswinkel et al. |

OTHER PUBLICATIONS

International Search Report for International Application No. PCT/EP2013/002670; dated Oct. 18, 2013; 7 pages.
Japanese Publication No. 11199357; Date of Publication: Jul. 27, 1999; Abstract Only, 1 page.

* cited by examiner

PROCESS FOR OLIGOMERIZATION OF ETHYLENE

CROSS REFERENCE TO RELATED APPLICATIONS

The present application is a 371 application of PCT/EP2013/002670, filed Sep. 5, 2013, which claims priority to European Application No. 12194589.3, filed Nov. 28, 2012, the contents of which are incorporated by reference in their entirety.

The present invention relates to a process for the oligomerization of ethylene.

Processes for the production of linear alpha olefins (LAOs), including comonomer-grade 1-hexene, are widely known and rely on the oligomerization of ethylene utilizing various catalyst compositions. These processes have in common that they lead to a product distribution of ethylene oligomers of chain length 4, 6, 8 and so on.

Further, catalyst compositions are known for oligomerization of ethylene which can predominantly prepare 1-hexene oligomers.

For example, US 2010/0190939 A1 discloses a catalyst composition comprising a chromium compound, a ligand of the general structure PNPN or PNPNP, and an activator or co-catalyst, which can be used in the oligomerization of ethylene to produce predominantly hexene oligomers.

Further, US 2012/0029258 A1 discloses a quite similar catalyst composition additionally comprising a modifier containing organic or inorganic halide, or a modifier containing a free amine group, respectively.

US 2010/0190939 A1 and US 2012/0029258 A1 describe both oligomerization reactions having a typical selectivity to 1-hexene of higher than 92 weight percent (1-hexene purity>99 weight percent), butenes≈3 weight percent, decenes≈5 weight percent, octenes≈0.5 weight percent and polymer ≈0.3 weight percent, all weight percentages are based on the total weight of the oligomers/polymers obtained. Typical process conditions for these oligomerization reactions are within the range of 10-100 bar pressure and 30 to 70° C. temperature.

The commercial processes for ethylene trimerization known in the art involve feeding a solvent, preferably toluene, ethylene recycle with fresh ethylene make-up, and the respective catalyst solution into a reactor, preferably a multi-tubular reactor, more preferably a bubble-column reactor. Un-reacted ethylene and light ends LAO that have partitioned into the vapour phase exit from the top of the reactor as reactor overhead effluent and are flashed to recover only ethylene, while the condensed LAO, here mostly $C_4$ and minor $C_6$, are combined with the liquid stream from the reactor bottom for further purification.

The bottom reactor effluents containing the LAO products (≥C4), together with dissolved ethylene, solvent and catalyst, are continuously withdrawn from the bottom of the reactor. Because the catalyst is still active, a quench medium, preferably n-decanol, is immediately added and blended with the reactor liquid effluents. This stream is sent to an ethylene recovery column where dissolved ethylene is recovered and recycled back into the reactor.

The bottom-ends of a C2 stripper comprising of LAOs, solvent, spent catalyst, quenching medium, is sent to a product recovery section, where it is fractionated in a series of about 4 to 5 distillation columns to individually separate butenes, hexenes, solvent, octenes, decenes and ≥C12 products, as well as polymers, etc.

A process known in the art is illustrated in FIG. 1. Into a reactor 1, solvent 2, catalyst 3 and ethylene 4 are entered via respective lines to conduct an oligomerization process. Gaseous reactor overhead effluent is removed from the reactor and transferred to an externally located cooling device 5, such as a condenser. Ethylene obtained is transferred back into the reactor, if necessary with a fresh ethylene make-up 6. Reactor bottom effluent is quenched with a quenching medium 7 and combined in mixer 14 with linear alpha-olefins liquefied in the cooling device 5. This quenched reactor bottom effluent is then sent to a series of fractionation columns 8-13. In the fractionation column 8, ethylene dissolved in the solvent is removed and separated, which can then be also recycled into the reactor. In fractionation column 9, butenes may be separated, while in the fractionation column 10, hexenes can be removed and further processed afterwards. If, for example, toluene is utilized as solvent in the oligomerization reaction, this can be separated in fractionation column 11, while higher linear alpha-olefins, i.e. octenes and decenes, can be individually separated in fractionation columns 12 and 13. Any further residues, such as ≥C12 fractions, spent catalyst, polymer materials and quench media can be further processed, which is not described here in detail.

Disadvantages of prior art processes for the oligomerization of ethylene are high capital and operational expenditures, for example the costs of several fractionation columns in the separation section for product recovery, the formation of heavy wax which results in fouling/plugging of reactor and reactor equipment, as well as the difficulty of heat removal for the exothermic oligomerization process.

It is thus an object of the present invention to overcome the disadvantages of the prior art, especially to provide a process for the oligomerization of ethylene having reduced capital and operational expenditure, reduced formation of heavy wax or easy removal thereof, as well as improved heat removal.

This object is achieved by a process for the oligomerization of ethylene, comprising the steps of:
a) oligomerizing of ethylene in a reactor in the presence of solvent and catalyst;
b) transferring reactor overhead effluent to an externally located cooling device and recycling condensed effluent into the reactor;
c) transferring the reactor bottom effluent to a series of fractionation columns and, in the following order,
   i) optionally separating a C4 fraction,
   ii) separating a C6 fraction,
   iii) simultaneously separating C8 and C10 fractions and recycling thereof into the reactor, and
   iv) separating residues comprising ≥C12 fractions, spent catalyst, polymer material and quench media, from the process,
wherein the solvent is separated in any of the steps i)-iv) and/or in an additional step.

It is obvious for someone skilled in the art that depending on the choice of a solvent, this can be removed at various positions. For example, if toluene is used as solvent, a solvent removal step between steps ii) and iii) is preferred. Solvents can be chosen so that the solvent removal step falls together with any of the steps i)-iv) or solvent can be chosen, like toluene, to add an additional step into the process.

While the condensed reactor overhead effluent as well as the C8 and C10 fractions are recycled into the reactor, all other fractions obtained can be further processed, as desired, but not recycled into the reactor. Especially the most preferably desired C6 fraction is further processed for purification to allow the use thereof, for example, in the copolymerization thereof with ethylene.

In one preferred embodiment, the catalyst comprises (1) a chromium compound, (2) a ligand of the general structure (A) $R_1R_2P$—$N(R_3)$—$P(R_4)$—$N(R_5)$—H or (B) $R_1R_2P$—N($R_3$)—P($R_4$)—N($R_5$)—$PR_6R_7$, wherein $R_1$, $R_2$, $R_3$, $R_4$, $R_5$, $R_6$ and $R_7$ are independently selected from halogen, amino, trimethylsilyl, C1-C10-alkyl, $C_6$-$C_{20}$ aryl and substituted $C_6$-$C_{20}$ aryl, and (3) an activator or co-catalyst.

In another preferred embodiment, the chromium compound is selected from the group consisting of $CrCl_3(THF)_3$, Cr(III) acetyl acetonate, Cr(III) octanoate, chromium hexacarbonyl, Cr(III)-2-ethyl hexanoate, benzene (tricarbonyl)-chromium, Cr(III) chloride.

Preferably, the activator or co-catalyst is selected from trimethyl aluminum, triethyl aluminum, triisopropyl aluminum, triisobutyl aluminum, ethylaluminum sesquichloride, diethyl aluminum chloride, ethyl aluminum dichloride, methyl aluminoxane (MAO) or mixtures thereof.

More preferred, the process is the trimerization of ethylene. As the process is preferably the trimerization of ethylene to result in the production of 1-hexene, a solvent should be chosen which is not simultaneously removed in the $C_6$ recovery step.

The reactor overhead transferred and recycled in step b) preferably comprises unreacted ethylene or unreacted ethylene and butenes.

The cooling device is preferably a condenser or a series of heat exchangers.

Preferably, the reactor overhead effluent is cooled in the cooling device to a temperature of −30° C. to +10° C., preferably −10° C. to +5° C., more preferably −5° C. to 0° C., and is then recycled into the reactor.

Make-up ethylene can be added to the condensed reactor overhead effluent to be recycled into the reactor.

The C8 and C10 fractions obtained in step iii) are preferably recycled into the reactor at a temperature of about 10-20° C.

The residue obtained in step iv) can be sent to incineration or is used as fuel in an adjacent plant.

The content of C4 in the reactor preferably is from 5 to 30 weight percent, the content of C8 is from 1 to 2 weight percent, and/or the content of C10 in the reactor is from 5-10 weight percent, all weight percentages given based on the total weight of liquids contained in the reactor.

Preferably, the total content of linear alpha-olefins in the liquid is from 30-75 wt. %, preferably 30-55 wt. % based on the total weight of liquids contained in the reactor. As can be taken from table 3, below, the total LAO content without ethylene (i.e. liquid product) is about 38%. Further, the LAO/solvent ratio is preferably about 50%.

Finally, the reactor may be a multi tubular reactor and/or a bubble column reactor.

Surprisingly, it was found that the process for the oligomerization of ethylene, preferably the trimerization of ethylene, according to the present invention provides reduced capital and operational expenditures, allows easy removal of heavy wax formed in the reactor or the reactor equipment, and improves heat removal of the exothermic oligomerization.

According to the present invention, the two separate distillation columns, each for C8 and C10 used in the art, are according to the present invention combined in one single column. This can be advantageously utilized as the process of the present invention is preferably chromium catalyzed and produces a very limited amount of other oligomers apart from C6. Saving one column definitely reduces the overall investment cost of the entire process.

Further, a major challenge in existing ethylene oligomerization processes is the efficient heat removal from the exothermal reaction. Some commercial processes use excessive ethylene to cool down the reactor to the desired temperature that favours catalyst activity and selectivity. However, with such excess ethylene, ethylene per pass conversion is very low for bubble column reactors resulting in significant load on C2 recovery column, hence higher operating costs. The inventive process can now be conceived wherein some of the heat of reaction is taken away by the latent heat of evaporation of condensed C2/C4 from the condenser bottom as well as from the sensible heat from heavy LAO that are routed back to the reactor.

Additionally, a well known inherent disadvantage of chromium-based ethylene oligomerization catalysts is the formation of heavy wax. This solid residue (mostly polyethylene and heavy waxes) tends to cause plugging/fouling inside the reactor and reactor equipment. This is especially the case in a bubble column reactor in which the condenser is located within the reactor.

In such designs, the internal condenser serves as additional surface for solid accumulations, such that the reactor needs to be periodically shut down for cleaning. Such a situation causes interruption to continuous operation. The inventive process overcomes this disadvantage and avoids any internals within the ethylene trimerization reactor, while at the same time providing same cooling capacity to maintain the reactor temperature and/or mobilizing the solid residues out of the reactor to reduce fouling.

The process of the present invention is practiced in a way that reactor plugging by polymer materials or waxes is significantly reduced by dissolving the polymer materials in higher fractions of C8 and C10 present within the reactor equipment. Polymer materials are known to be more soluble in heavier than lighter-end olefins. By recycling C8 and C10 fractions into the reactor, the time-on stream of the inventive process can be significantly prolonged. Further, the inventive process can be operated at a reduced temperature by adjusting the reactor content in view of both fractions, C8 and C10, which also enhances ethylene solubility. This will potentially benefit catalyst activity as well.

In a preferred embodiment, if condensed C2 and C4 is sent to the reactor as liquid rather than as gaseous streams, this will significantly enhance the cooling of the oligomerization reactor by utilizing significant portion of heat of reaction as latent heat of evaporation.

Figure 2:
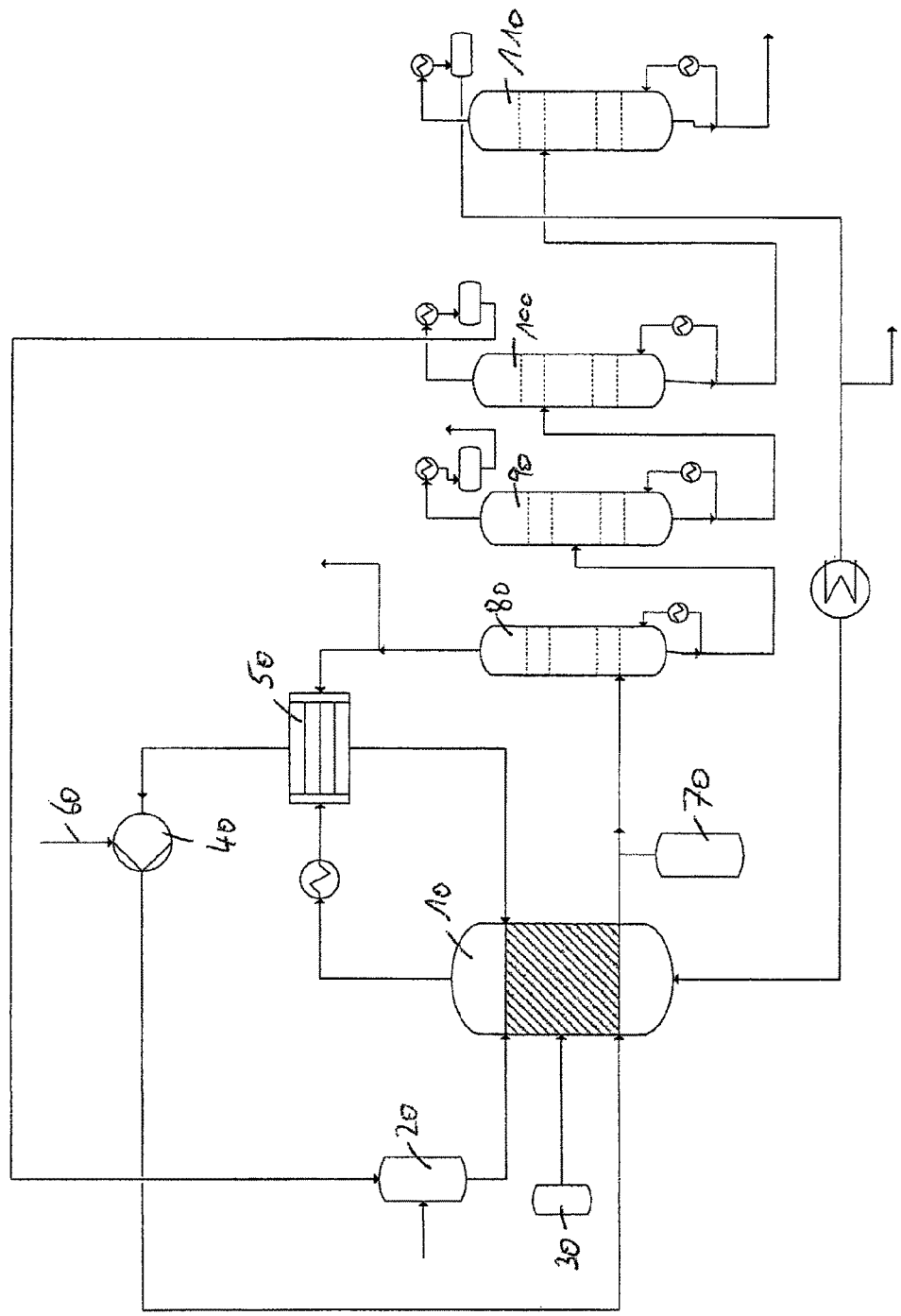

Additional advantages and features of the inventive process can be taken from the following detailed description of a preferred embodiment, together with the drawings, wherein FIG. 1 discloses a schematic illustration of a state of the art commercial process for oligomerization; and FIG. 2 is a schematic illustration of the process of the present invention.

As for the process illustrated in FIG. 1, also in FIG. 2 solvent 20 (optionally with fresh make-up solvent), catalyst 30 and ethylene 40 (optionally with fresh make-up ethylene 60) are entered into a reactor 10 for oligomerization. Reactor overhead effluent, preferably containing ethylene and butenes, is transferred to an externally located cooling device 50 and is recycled, either with fresh make-up ethylene or directly, into the reactor 10. Reactor bottom effluent is discharged from the reactor 10 and transferred to a quenching unit 70 where quenching medium is added. The quenched reactor bottom effluent is then transferred to a series of fractionation columns 80-110, wherein in the first fractionation column 80 ethylene dissolved in the solvent and butenes are separated jointly and transferred to the cooling device 50 to be finally recycled into the reactor 10. In fractionation column 90, hexenes are separated and discharged for further processing. If, for example, toluene is used as solvent, this can be removed and separated in fractionation column 100. Finally, C8 and C10 fractions are removed and separated simultaneously (jointly) in fractionation column 110. C8 and C10 fractions are recycled into the reactor 10, while any further residues can be then transferred for further processing.

Illustrative Embodiments

A multi compartment reactor model was developed to account for detailed hydrodynamics, thermodynamics and the variable gas flow-rate resulting from chemical/physical contraction, and gas/liquid re-circulation in a bubble-column reactor. The reactor model was coupled to a mechanistic kinetic model developed specifically for the novel ethylene trimerization catalyst system described by US 20120029258. The model was used to analyze one embodiment of the present invention. The performance of a pilot-scale bubble-column reactor for ethylene trimerization process for this embodiment of the present invention was verified with the developed rigorous reactor model.

Further, a comparative example is provided illustrating a process for oligomerization known in the art, however utilizing an externally located condenser with a total reflux to separate unconverted ethylene from reactor top effluents. The separated ethylene is combined with make-up ethylene and ethylene from C2 column, which is recycled back to the reactor. Hence, in this comparative example, the feed gas composition is mostly ethylene, i.e., 98-99 wt. % C2. 1-butene is not present in the ethylene recycle stream, nor is there any recycling of C8 and C10 fractions into the reactor.

COMPARATIVE EXAMPLE

The stream analysis from the comparative example 1 is presented in Table 1. Process key performance indicators (KPIS) are shown in Table 2.

TABLE 2

| | |
|---|---|
| Ethylene conversion | 0.0627512 |
| Selectivity ("1-BUTENE") | 0.0248341 |
| Selectivity ("1-HEXENE") | 0.941373 |
| Selectivity ("1-OCTENE") | 1.61962E−11 |
| Selectivity ("1-DECENE") | 0.0337925 |
| Selectivity ("1-DODECENE") | 3.78892E−11 |
| Heat of reaction (kW) | 5.02985 |
| Condenser duty (kW) | −7.54554 |
| Catalyst mole fraction in liquid feed | 0.000200259 |
| Condenser temperature | 271.150 |

As shown in Table 2, ethylene per pass conversion of ~6 wt % was obtained with the condenser duty of −7.5 kW operated at −2° C.

INVENTIVE EXAMPLE

Ethylene and 1-butene are sent directly to the externally located condenser after passing through an heat exchanger to reduce temperature to about 35° C. The condensed ethylene/1-butene enters the reactor as liquid streams preferably from the top of a disengagement zone, even more preferably from the side towards the reaction zone for effective cooling. The ethylene/1-butene content in the reactor can be maintained between 5-30 wt % via a purge stream.

Similarly, decenes/1-octene from the top of $1\text{-}C_8/C_{10}$ fractionation column are routed back to the reactor after been cooled from 170° C. to 10~20° C. The decenes content in the reactor can be maintained between 5-10% via a purge stream. Additional duty to cool the recycled $1\text{-}C_8/C_{10}$ to lower temperatures may have to be considered. Notwithstanding, the extra benefits provided by the recycled heavy fraction for polymer mobilization and reactor cooling in form of sensible heats may offset this duty.

Table 3 shows the stream analysis, while Table 4 illustrates the key process indicators for this inventive process.

TABLE 1

Stream analysis for the comparative example with an overhead condenser having total reflux and without $C_4$ recycle

| | Source_Gas (Feed gas) | Source_Liquid (Liq_in) | Sink-Liquid (Liq products) | Sink_Gas (gas_products) | Condenser (Flow_in) | Condenser (Liq_out) |
|---|---|---|---|---|---|---|
| Molare flowrate (kmol/hr) | 4.19 | 0.09 | 0.41 | 3.70 | 5.19 | 1.49 |
| Temperature (K) | 308.15 | 294.15 | 323.15 | 271.15 | 323.09 | 271.15 |
| Pressure (bar) | 30.00 | 30.00 | 29.97 | 29.97 | 29.97 | 29.97 |
| TOLUENE (mol/mol) | 0.00 | 1.00 | 0.21 | 0.00 | 0.00 | 0.01 |
| ETHYLENE (mol/mol) | 0.98 | 0.00 | 0.47 | 0.99 | 0.95 | 0.85 |
| 1-BUTENE (mol/mol) | 0.02 | 0.00 | 0.12 | 0.01 | 0.04 | 0.12 |
| 1-HEXENE (mol/mol) | 0.00 | 0.00 | 0.20 | 0.00 | 0.01 | 0.02 |
| 1-OCTENE (mol/mol) | 0.00 | 0.00 | 0.00 | 0.00 | 0.00 | 0.00 |
| DECENES (mol/mol) | 0.00 | 0.00 | 0.00 | 0.00 | 0.00 | 0.00 |
| DODECENES (mol/mol) | 0.00 | 0.00 | 0.00 | 0.00 | 0.00 | 0.00 |

TABLE 3

Stream analysis for the preferred embodiment of present invention with
$C_2/C_4$ as recycled as liquid streams and 1-octene/decenes recycled

|  | Source_Gas (Feed gas) | Source_Liquid (Liq_in) | Sink-Liquid (Liq products) | Sink_Gas (gas_products) | Condenser (Flow_in) | Condenser (Liq_out) |
|---|---|---|---|---|---|---|
| Molare flowrate (kmol/hr) | 1.77 | 0.09 | 0.47 | 3.02 | 1.52 | 0.27 |
| Temperature (K) | 308.15 | 294.15 | 323.15 | 314.34 | 274.15 | 308.15 |
| Pressure (bar) | 30.00 | 30.00 | 29.96 | 29.96 | 29.96 | 30.00 |
| TOLUENE (mol/mol) | 0.00 | 0.93 | 0.17 | 0.00 | 0.00 | 0.00 |
| ETHYLENE (mol/mol) | 0.99 | 0.00 | 0.46 | 0.90 | 0.81 | 0.59 |
| 1-BUTENE (mol/mol) | 0.01 | 0.00 | 0.19 | 0.10 | 0.17 | 0.40 |
| 1-HEXENE (mol/mol) | 0.00 | 0.00 | 0.17 | 0.01 | 0.01 | 0.02 |
| 1-OCTENE (mol/mol) | 0.00 | 0.00 | 0.00 | 0.00 | 0.00 | 0.00 |
| DECENES (mol/mol) | 0.00 | 0.07 | 0.02 | 0.00 | 0.00 | 0.00 |
| DODECENES (mol/mol) | 0.00 | 0.00 | 0.00 | 0.00 | 0.00 | 0.00 |

TABLE 4

| Ethylene conversion | 0.0773188 |
|---|---|
| Selectivity ("1-BUTENE") | 0.0251504 |
| Selectivity ("1-HEXENE") | 0.946202 |
| Selectivity ("1-OCTENE") | 3.85301E−12 |
| Selectivity ("1-DECENE") | 0.0286475 |
| Selectivity ("1-DODECENE") | 3.35246E−12 |
| Heat of reaction (kW) | 4.52678 |
| Condenser duty (kW) | −5.26443 |
| Catalyst mole fraction in liquid feed | 0.000170544 |
| Condenser temperature | 274.150 |

As shown in the illustrative example, ethylene per pass conversion is ~8% with condenser duty of −5 kW operated at 1° C. This embodiment typify the lower ethylene feed rate at 50 kg/hr.

The features of the invention disclosed in the above description and in the claims can be essential to implementing the invention in its various embodiments both individually and in any combination.

The invention claimed is:

1. A process for oligomerizing ethylene, comprising:
   a) oligomerizing ethylene in a reactor in the presence of a solvent and a catalyst;
   b) transferring a reactor overhead effluent from the reactor to an externally located cooling device to condense a portion of the reactor overhead effluent and recycling the condensed portion of the reactor overhead effluent into the reactor;
   c) recovering a reactor bottom effluent from the reactor, wherein the reactor bottom effluent comprises C4 hydrocarbons, C6 hydrocarbons, C8 hydrocarbons, C10 hydrocarbons, residual C12+ hydrocarbons, residual spent catalyst, and residual polymer material;
   d) transferring the reactor bottom effluent to a quenching unit, wherein quench media is added to the reactor bottom effluent, to produce a quenched reactor bottom effluent;
   e) transferring the quenched reactor bottom effluent to a series of fractionation columns and, in the following order,
      i) optionally separating a fraction comprising the C4 hydrocarbons from the quenched reactor bottom effluent;
      ii) separating a fraction comprising the C6 hydrocarbons from the quenched reactor bottom effluent;
      iii) separating a fraction comprising both the C8 hydrocarbons and C10 hydrocarbons from the quenched reactor bottom effluent and recycling said fraction comprising both the C8 hydrocarbons and C10 hydrocarbons into the reactor, and
      iv) separating the residual C12+ hydrocarbons, the residual spent catalyst, the residual polymer material, and residual quench media from the quenched reactor bottom effluent,
   wherein the solvent is separated from the quenched reactor bottom effluent in any of steps i)-iv) and/or in an additional step.

2. The process according to claim 1, wherein the catalyst comprise (1) a chromium compound, (2) a lingand of the general structure (A) $R_1R_2P$—$N(R_3)$—$P(R_4)$—$N(R_5)$—H or (B) $R_1R_2P$—$N(R_3)$—$P(R_4)$—$N(R_5)$—$PR_6R_7$, wherein $R_1$, $R_2$, $R_3$, $R_4$, $R_5$, $R_6$ and $R_7$ are independently selected from halogen groups, amino groups, a trimethylsilyl group, $C_1$-$C_{10}$ alkyl groups, $C_6$-$C_{20}$ aryl groups, and substituted $C_6$-$C_{20}$ aryl groups, and (3) an activator or co-catalyst.

3. The process according to claim 2, wherein the chromium compound is selected from the group consisting of $CrCl_3(THF)_3$, Cr(III) acetyl acetonate, Cr(III) octanoate, chromium hexacarbonyl, Cr(III)-2-ethyl hexanoate, benzene (tricarbonyl)-chormium, and Cr(III) chloride.

4. The process according to claim 2, wherein the activator or co-catalyst is selected from trimethyl aluminum, triethyl aluminum, triisopropyl aluminum, triisobutyl aluminum, ethylaluminum sesquichloride, diethyl aluminum chloride, ethyl aluminum dichloride, methyl aluminoxane (MAO) or mixtures thereof.

5. The process according to claim 1, wherein oligomerizing ethylene comprises trimerizing ethylene.

6. The process according to claim 1, wherein the condensed portion of the reactor overhead effluent recycled to the reactor comprises unreacted ethylene.

7. The process according to claim 1, wherein the condensed portion of the reactor overhead effluent is at a temperature of −30° C. to +10° C. prior to being recycled into the reactor.

8. The process according to claim 1, wherein make-up ethylene is added to the condensed portion of the reactor overhead effluent to be recycled into the reactor.

9. The process according to claim 1, wherein the fraction comprising both the C8 hydrocarbons and C10 hydrocarbons obtained in step iii) is recycled into the reactor at a temperature of about 10-20° C.

10. The process according to claim 1, wherein the content of C4 hydrocarbons in the reactor is from 5 to 30 weight percent, the content of C8 hydrocarbons in the reactor is from 1 to 2 weight percent, and/or the content of C10 hydrocarbons in the reactor is from 5 to 30 weight percent, where all weight percentages are based on the total weight of liquids contained in the reactor.

11. The process according to claim 1, wherein the total content of linear alpha-olefins in the reactor is from 30 to 75 weight percent based on the total weight of liquids contained in the reactor.

12. The process according to claim 1, wherein the reactor is a multi tubular reactor and/or a bubble column reactor.

* * * * *